US007132236B2

(12) United States Patent
Sana et al.

(10) Patent No.: US 7,132,236 B2
(45) Date of Patent: Nov. 7, 2006

(54) COMPOSITION AND METHOD FOR OPTIMIZED HYBRIDIZATION USING MODIFIED SOLUTIONS

(75) Inventors: Theodore R. Sana, Santa Clara, CA (US); Paul K. Wolber, Los Altos, CA (US); Clotilde S. Perbost, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 34 days.

(21) Appl. No.: 10/001,688

(22) Filed: Oct. 25, 2001

(65) Prior Publication Data

US 2003/0104396 A1   Jun. 5, 2003

(51) Int. Cl.
*C12Q 1/68* (2006.01)
*C12Q 1/58* (2006.01)
*G01N 33/00* (2006.01)

(52) U.S. Cl. ............................ 435/6; 435/91.2; 435/12; 436/182; 436/106

(58) Field of Classification Search .................... 435/6, 435/91.2, 12; 536/25.4, 24.5; 436/108, 436/182

See application file for complete search history.

(56) References Cited

U.S. PATENT DOCUMENTS

| | | | |
|---|---|---|---|
| 5,547,860 | A | 8/1996 | Kocher et al. |
| 5,604,097 | A * | 2/1997 | Brenner .......................... 435/6 |
| 5,800,984 | A | 9/1998 | Vary |
| 5,985,567 | A | 11/1999 | Rampal |
| 6,177,248 | B1 | 1/2001 | Oliner et al. |
| 6,203,989 | B1 | 3/2001 | Goldberg et al. |
| 6,221,589 | B1 | 4/2001 | Lane et al. |
| 6,252,059 | B1 | 6/2001 | McDonough et al. |
| 6,262,216 | B1 | 7/2001 | McGall |
| 6,316,609 | B1 | 11/2001 | Dillon et al. |
| 6,322,989 | B1 | 11/2001 | Cohen |

FOREIGN PATENT DOCUMENTS

| | | |
|---|---|---|
| EP | 0 127 327 | 12/1984 |
| WO | WO97/43450 | 11/1997 |
| WO | WO01/66804 | 9/2001 |

OTHER PUBLICATIONS

Kourilsky et al., DNA-RNA hybridization at low temperature in the presence of urea, Biochemical and Biophysical Research, 1970, vol. 41(4), p. 1080-1087.*
Kourilsky et al., 1971, Biochimie, vol. 53, p. 1111-1114.*
Oliva et al, Bio Techniques, 2001, vol. 31(1), p. 74-76 and 78-81.*
Shchepinov, M.S., et al., "Steric Factors Influencing Hybridisation Of Nucleic Acids To Oligonucleotide Arrays", Nucleic Acids Research, 1977, vol. 25, No. 6, pp. 1155-1161.
Blanchard, A.P., et al., "High-Density Oligonucleotide Arrays", Biosensors & Bioelectronics, 1996, vol. 11, No. 6/7, pp. 687-690.
Wetmur, J.G., "Acceleration Of DNA Renaturation Rates", Biopolymers, 1975, vol. 14, pp. 2517-2524.
Hughes, T.R., et al., "Expression Profiling Using Microarrays Fabricated By An Ink-Jet Oligonucleotide Synthesizer", Nature Biotechnology, Apr. 2001, vol. 19, pp. 342-347.
Lockhart, D.J. et al., "Expression Monitoring By Hybirdization To High-Density Oligonucleotide Arrays", Nature Biotechnology, Dec. 1996, vol. 14, pp. 1675-1680.
Marton, M.J. et al., "Drug Target Validation And Identification Of Secondary Drug Target Effects Using DNA Microarrays", Nature Medicine, Nov. 1998, vol. 4, pp. 1293-1301.
Guo, Z., et al., "Direct Fluorescence Analysis Of Genetic Polymorphisms By Hybridization With Oligonucleotide Arrays On Glass Supports", Nucleic Acids Research, 1994, vol. 22, pp. 5456-5465.
DeRisi, J.L., et la. "Exploring The Metabolic And Genetic Control Of Gene Expression On A Genomic Scale", Science, Oct. 1997, vol. 278, pp. 680-686.
Sambrook, J., et al., "Hybridization To Nitrocellulose Filters Containing Replicas Of Bacterial Colonies", Molecular Cloning-A Labortory Manual, Second Edition, 1989, pp. 1.101-1.104.
Cantor, C. R., et al., "The Conformation Of Biological Macromolecules", Biophysical Chemistry, Part 1, 1980, pp. 176-184.
Kourilsky et al., Title: "DNA-DNA Hybridization on filters at low temperatures in the presence of formamide or urea", vol. 53, 1971, pp. 1111-1114.
Simard et al., Title: "Urea Substitutes toxic formamide as destabilizing agent in nucleic acid hybridizations with RNA probes", Electrophoresis, vol. 22, Aug. 2001, pp. 2679-2683.
European Search Report Dated Oct. 17, 2003.
J. Sambrook, E.F. Fritsch, T. Maniatis, "Molecular Cloning: A Loboratory Manual", Cold Spring Harbor Laboratory Press, Cold Spring Harbor, Ed. 2nd, 1989, pp. 1111.45-1111.61.
Ralph K. ller, "The Chemistry of Silica", John Wiley & Sons, N.Y., 1979, pp. 62-77.
E.F. Vansant et al., "Characterization and Chemical Modification of the Silicia Surface", Elsevier, New York, 1995, pp. 149-192.
J.J. Kirland et al., "Stability of Silica-based, encapped columns with pH 7 and 11 mobile phases for reversed-phase high-performance liquid chromatography", Journal of Chromatography A, 762 (1997) pp. 97-112.

* cited by examiner

*Primary Examiner*—Kenneth R. Horlick
*Assistant Examiner*—Joyce Tung

(57) ABSTRACT

The invention provides a composition, kit and method for hybridizing a probe and target at a temperature lower than their standard hybridization temperature. The chemical component added to the composition has a formula $R(NH_2)C{=}O$, where R is amino or alkyl. A method for use of the chemical component and composition is also disclosed.

13 Claims, 8 Drawing Sheets
(7 of 8 Drawing Sheet(s) Filed in Color)

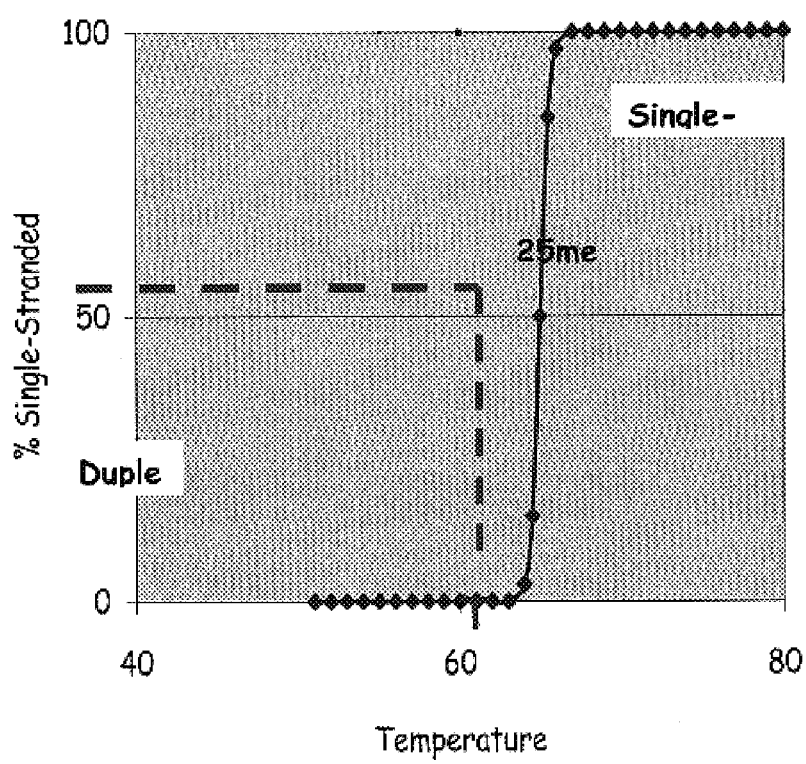
FIG. 3 Duplex Denaturation Curve
The stability of the duplex formed upon hybridization can be expressed as a function of the temperature in which 50% of the molecules are hybridized (Tm)

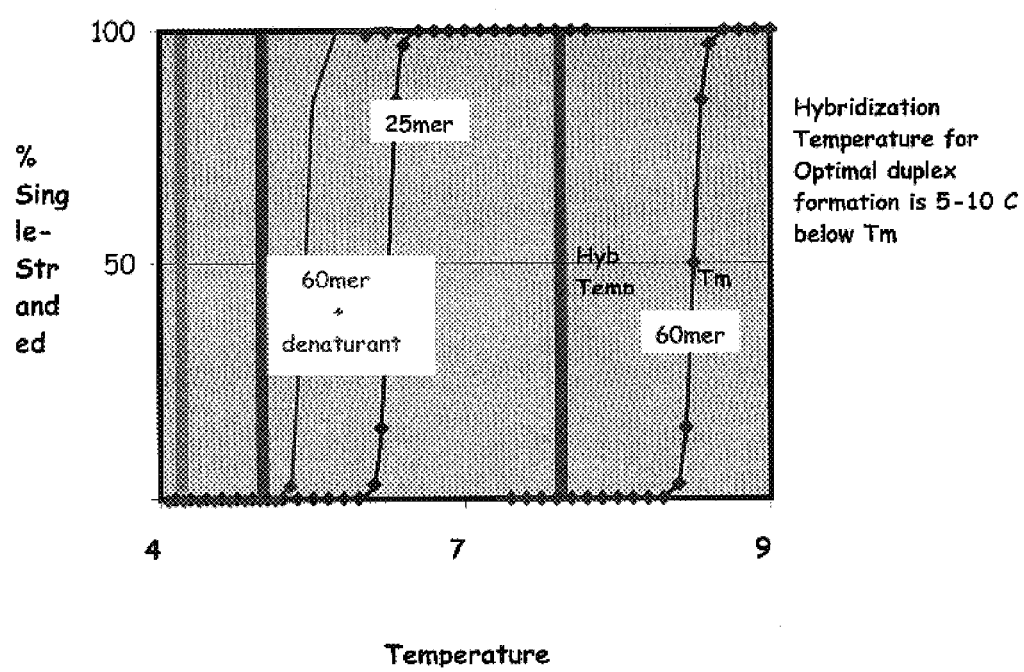
FIG. 4 Melting curves for 25, 60 and 60 mer with denaturant

FIG. 5 Extrapolation to Predicted Optimum for L=60 (50°C)
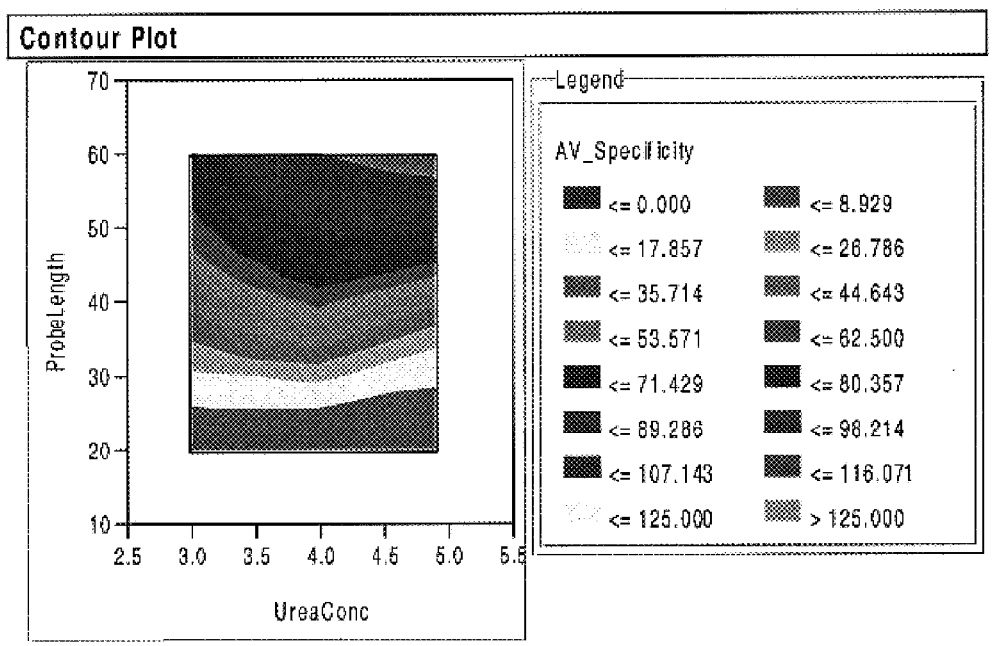

FIG. 6 Optimal Urea Concentrations of 50°C Probe Length Series
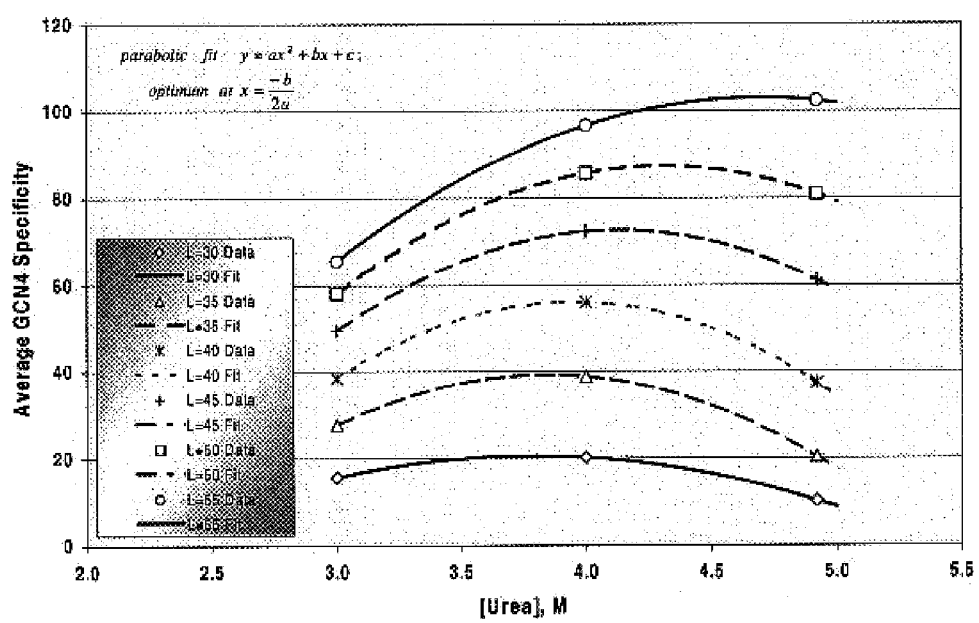

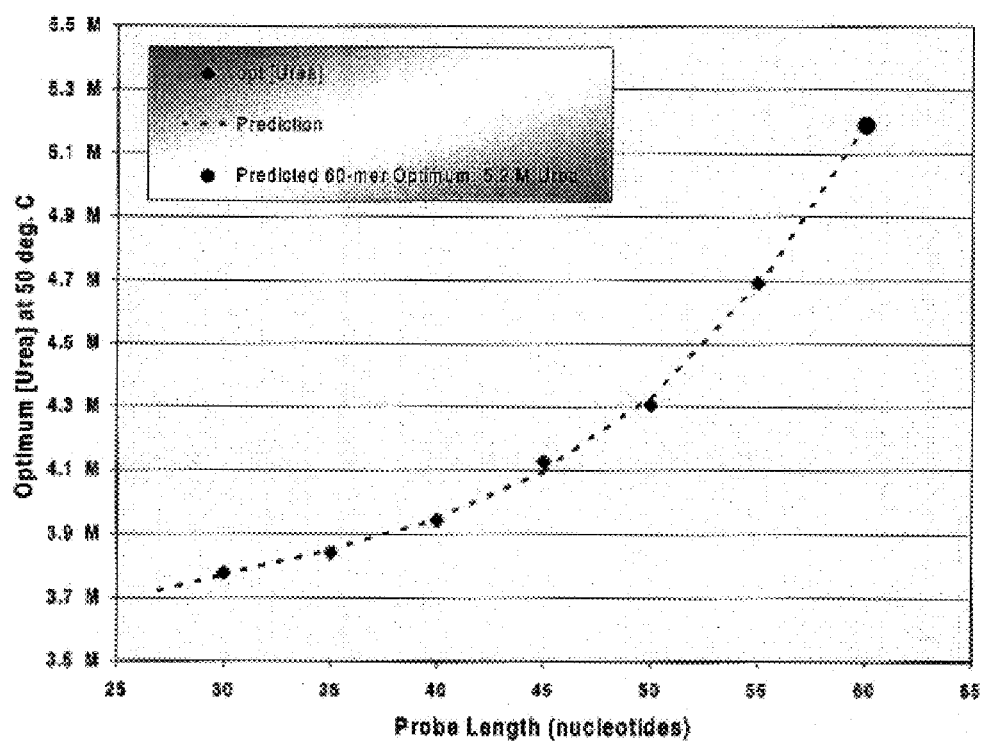
FIG. 7 Extrapolated Optimal [Urea] for L=60, T=50°C

FIG. 8 Extrapolation to Predicted Optimum for L=60 (50°C)
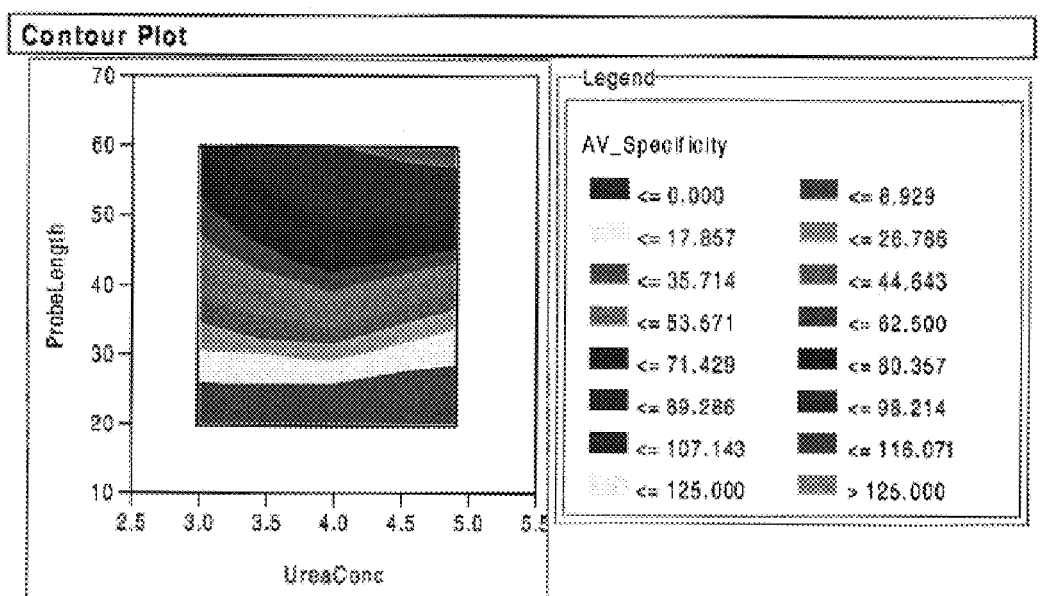

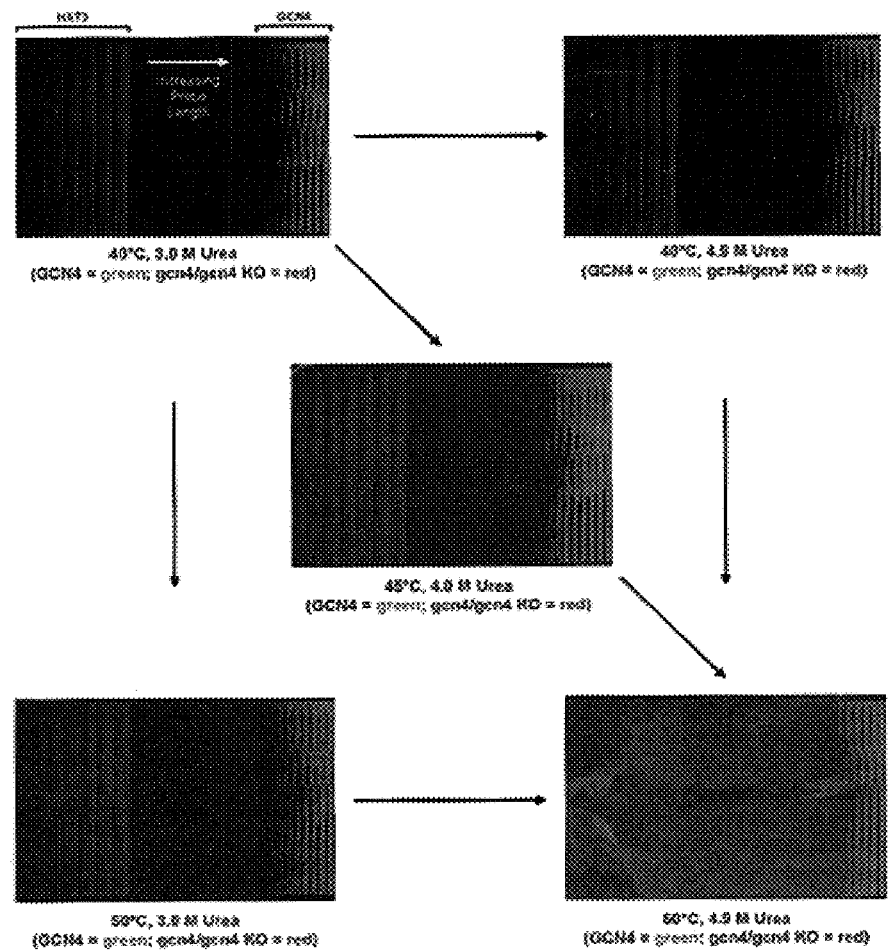
FIG. 9 Various Arrays Showing The Addition of The Denaturant

COMPOSITION AND METHOD FOR OPTIMIZED HYBRIDIZATION USING MODIFIED SOLUTIONS

FIELD OF THE INVENTION

The present invention relates to the field of nucleic acids and more particularly to a modified solution containing a denaturant for application with biopolymers and micro arrays.

BACKGROUND OF THE INVENTION

Various arrays of polynucleotides (such as RNA and DNA) are known and used in genetic testing, screening and diagnostics. Arrays are defined by the regions of different biopolymers or nucleotides arranged in a predetermined configuration on a substrate. Most importantly, the arrays when exposed to a population of analytes will exhibit a pattern indicative of the presence of the various components separated spatially. Array binding patterns of polynucleotides and/or peptides can be detected by using a variety of suitable target labels. Once bound to the array, these target labels can then be quantified and observed and the overall pattern on the array determined.

DNA micro arrays are particularly useful for analyzing large sets of genes through "gene expression profiling". However, for the micro arrays to be effective in binding target sequences, they must be capable of annealing. In addition, the detection of optimal "sensitivity" and "specificity" of hybridization for biopolymers (probes) to complimentary sequences in complex cRNA is complicated by the fact that the characteristic melting temperature (Tm) for this interaction rises with increasing probe length. However, increasing the stringency of hybridization comes with the cost of losing sensitivity. Moreover, the higher temperatures needed to reach the Tm (>60° C.) are detrimental to the array surface. Previous researchers have determined that including 30% formamide in the hybridization solution can significantly reduce the Tm and allow for hybridization to take place at a lower temperature while maintaining an acceptable balance between specificity and sensitivity. Formamide is often used in Southern and Northern blotting as a hybridization modifier, because it is effective and because it is easily washed out of the nitrocellulose or modified nylon materials used to perform porous filter-based hybridization assays. However, formamide is a highly toxic and hazardous to ship (the US Department of Transportation requires double-containment of formamide-containing solutions). For these reasons it would be desirable to create an effective solution system that maintains specificity, sensitivity and allows for hybridizations at lower temperature, yet is not toxic, does not effect the central nervous system of the operator, is not a fetal poison or does not require special handling or transportation costs. These and other problems with the prior art systems and solutions are obviated by the present invention. The references cited in this application infra and supra, are hereby incorporated by reference. However, cited references or art are not admitted to be prior art to this application.

SUMMARY OF THE INVENTION

The invention provides a composition, kit and method for use with micro arrays. The composition, kit and method allow a probe and target to hybridize at a temperature lower than their standard hybridization temperature. The composition has a chemical component of the formula:

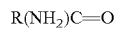

$$R(NH_2)C=O$$

where R is an amino or alkyl group. The kit of the present invention comprises a micro array, a composition for use with the micro array and a target for detection. The kit may further comprise an optional set of instructions. The composition in the kit contains the chemical component. The chemical component may or may not be in solution. The method provides the steps of adding to a probe and target the chemical component, heating the probe and target in the presence of the added component and then allowing the biopolymers to hybridize.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention will now be described with reference to the drawings in which:

FIG. 3 shows a duplex hybridization curve without the addition of the denaturant. Percentage of single stranded DNA is plotted against temperature.

FIG. 4 shows a plot of percentage of single stranded DNA against temperature. The plot shows a series of melting curves (25, 60 and 60 mer with denaturant added).

FIG. 5 shows a contour plot of the observed optimal conditions using urea concentrations with varying probe lengths (L=60, T=50° C.). Probe length has been plotted against urea concentration.

FIG. 6 shows a plot of optimal urea concentrations of 50° C. probe length series. The plot shows average GCN4 specificity plotted against urea concentration.

FIG. 7 shows the extrapolated optimal urea concentration for a probe length of 60-mer at a temperature of 50° C. Optimum urea concentration at 50° C. is plotted against probe length.

FIG. 8 shows a contour plot of the extrapolation to predicted optimum for the probe having a length of 60 and 50° C. Probe length has been plotted against urea concentration.

FIG. 9 shows the results of various arrays with the addition of the denaturant.

DETAILED DESCRIPTION OF THE INVENTION

Figure 1:
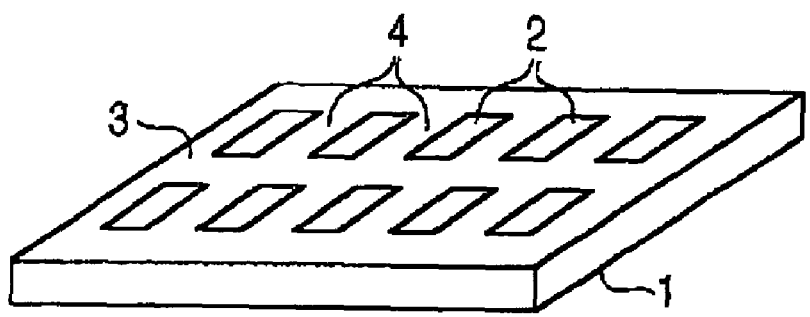
FIG. 1 illustrates a single nucleotide polymorphic array.

Before describing the present invention in detail, it is to be understood that this invention is not limited to specific compositions, process steps, or equipment, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "an array" includes more than one array, reference to "a polynucleotide primer" includes a plurality of polynucleotide primers and the like.

In describing and claiming the present invention, the following terminology will be used in accordance with the definitions set out below.

A "biopolymer" is a polymer of one or more types of repeating units. This includes traditional polynucleotides, the case in which the conventional backbone has been replaced with a non-naturally occurring or synthetic backbone, and nucleic acids in which one or more of the conventional bases have been replaced with a synthetic base capable of participating in Watson-Crick type hydrogen bonding interactions. Polynucleotides include single or multiple stranded configurations, where one or more of the strands may or may not be completely aligned with another. While probes and targets of the present invention will typically be single-stranded, this is not essential. Specifically, a "biopolymer" includes DNA (including cDNA), RNA and polynucleotides, regardless of the source.

An "alkyl" group includes aliphatic and aromatic hydrocarbon molecules as well as substituted hydrocarbons and their derivatives.

A "nucleotide" refers to a sub-unit of a nucleic acid and has a phosphate group, a 5-carbon sugar and a nitrogen containing base, as well as analogs of such sub-units. An "oligonucleotide" generally refers to a nucleotide multimer of about 10 to 100 nucleotides in length, while a "polynucleotide" includes a nucleotide multimer having any number of nucleotides.

An "array" or "micro array", unless a contrary intention appears, includes any one or two dimensional arrangement(s) of addressable regions bearing particular biopolymer moieties (for example different polynucleotide sequences) associated with that region. An array is "addressable" in that it has multiple regions of different moieties (for example, different sequences) such that a region at a predetermined location (an "address") on the array (a "feature" of the array) will detect a particular target or class of targets (although a feature may incidentally detect non-targets of the feature). In the present case, the polynucleotide (or other) target will be in a mobile phase (typically fluid), while probes for the target ("probes") may or may not be mobile. "Hybridizing", "annealing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" is a particular sub-class of binding efficiency, and refers to binding efficiency in the case where the binding components are polynucleotides The term "Fluid" is used herein to reference to a liquid.

The term "target" shall refer to a nucleic acid, nucleotide, nucleoside or their analogs. The term shall also include nucleotides having modified sugars as well as organic and inorganic leaving groups attached to the purine or pyrimidine rings.

The term "probe" shall refer to a biopolymer such as a nucleic acid, nucleotide, nucleoside or their analogs. The term shall also include nucleotides having modified sugars as well as organic and inorganic leaving groups attached to the purine or pyrimidine rings.

The term "specificity" shall refer to a ratio of specific to non-specific hybridization.

The term "sensitivity" shall refer to signal intensity of a molecule that may or may not be attached to a micro array surface.

The term "channel" shall refer to an area on an array that defines a particular type of feature of the array.

The term "stringent" or "stringency" shall refer to any condition or parameter imposed on a system or hybridization of probe and target that improves results (i.e. addition of a denaturant to increase hybridization efficiency).

The term "standard hybridization temperature" shall refer to the temperature at which two oligonucleotides (i.e. a probe and target) anneal without the addition of any denaturant or other component(s). This is the hybridization temperature of the nucleic acids without any other components that effect the system thermodynamically. It is also related to a prescribed amount of heat and/or quantum of energy that is added to a closed system to produce a prescribed level of entropy and Watson-Crick base pairing.

Figure 2:
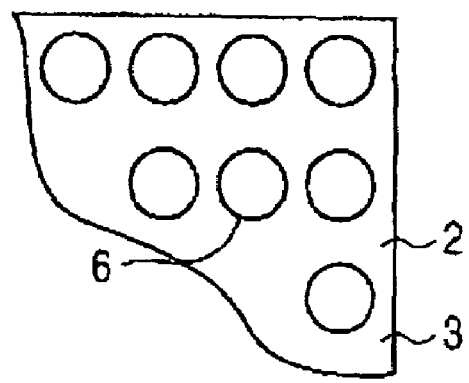
FIG. 2 is an enlarged view of a portion of FIG. 1 showing multiple spots or regions of an array.

Referring first to FIGS. 1–3, typically kits and methods of the present invention use a contiguous substrate 1 carrying arrays 2 disposed across an array surface 3 of substrate 1 and separated by interfeature areas 4. The arrays on substrate 1 can be designed for testing an analyte or for evaluating probes on their ability to form hybrids. While a number of arrays 2 are displayed and shown in FIG. 1, the different embodiments described below may use substrates with particular numbers of arrays, it will be understood that substrate 1 and the embodiments to be used with it may use any number of desired arrays 2. For instance, substrate 1 may carry at least one, two, four, or at least ten arrays 2. Depending upon the intended use, any or all the arrays 2 may be the same or different from one another and each may contain multiple spots or features 6 of biopolymers. A typical array may contain more than ten, more than one hundred, more than one thousand or ten thousand features, or even more than one hundred thousand features in an area of less than 20 cm$^2$ or even less than 10 cm$^2$. For example, features may have widths (that is, diameter, for a round spot) in the range from a 10 μm to 1.0 cm. In other embodiments each feature 6 may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges.

Some or all of the features 6 may be of different compositions. As mentioned, interfeature areas 4 will typically (but not essentially) be present which do not carry any polynucleotide (or other biopolymer of a type of which features 6 are composed). Interfeature areas 4 typically will be present where arrays 2 are formed by the conventional in situ process or by deposition of previously obtained moieties, as described above, by depositing for each feature at least one droplet of reagent such as from a pulse jet (for example, an inkjet type head). It will be appreciated though, that the interfeature areas 4, when present, could be of various sizes and configurations. It will also be appreciated that there need not be any space separating arrays 2 from one another. Each feature 6 carries a predetermined polynucleotide (which includes the possibility of mixtures of polynucleotides). As per usual, A, C, G, T represent the usual nucleotides. It will be understood that there is usually a linker molecule (not shown) of any known types between the front surface and the first nucleotide.

FIGS. 1–2 illustrate an ideal array where actual features 6 are the same as the target (or desired) features, with each feature 6 being uniform in shape, size and composition, and the features 6 being regularly spaced. Such an array when fabricated by drop deposition methods, would require all reagent droplets for each feature to be uniform in shape and accurately deposited at the target feature location. In practice, such an ideal result is difficult to obtain due to fixed and random errors during fabrication. Substrate 1, may have a thickness of less than 1 cm, or even less than 5 mm, 2 mm, 1 mm, or in some embodiments even less than 0.5 mm or 0.2 mm. In the situation where the array is read by detecting fluorescence, substrate 1 may be of a material that emits low fluorescence upon illumination with the excitation light. The figures and description should not be interpreted as limiting the scope of the invention and are for illustrative purposes only. The invention has application to variety of micro array designs that allow biopolymers to hybridize. Similarly, substrate 1 may be of any shape, and any apparatus used with it adapted accordingly.

It should be noted that an important part of the arrays 2 is the ability of the attached polynucleotides to hybridize to a known or unknown target 7 (not shown in FIGS.). Hybridization occurs by annealing of complementary strands. The kinetics of hybridization are well known in the art and studied. For instance, the kinetics of hybridization for an immobilized target can be defined by:

$$k1[Cf][Cs]$$

where k1 is a constant, [Cf] is the concentration of the bound target sequence, a constant, [Cs] is the concentration of oligonucleotide in solution. However, a number of experiments have shown that hybridization depends on two processes; diffusion of the probe to the site and hybridization at the site. Therefore, the above equation can be written and more accurately defined by:

$$k1[Cf][Cs]+J$$

where J is the diffusion coefficient of the probe. From this equation it follows that when the [Cf] is low, the hybridization is limiting and when the concentration of [Cf] is high the diffusion is limiting.

Referring now to FIG. 3, a standard annealing curve is shown. The figure shows a duplex denaturation curve in which percentage of single stranded DNA is plotted against temperature. No denaturant has been added to the DNA. Complementary oligonucleotides are present in solution. The plot shows that as the temperature is increased the probability of annealing is increased. This is probably due to the increased energy that is added to the oligonucleotide chains in the form of heat. The chains begin to rotate and move in solution increasing the probability of complementary strands and bases to pair and hybridize to form more stable structures. The hybrization temperature is marked by the vertical line in the graph where the stability of the duplex formed upon hybridization can be expressed as a function of the temperature in which 50% of the molecules are hybridized (Tm).

A molecule such as urea can be used in annealing or hybridizations reactions to lower the Tm. This is particularly effective in annealing DNA, RNA as a target and especially with dsRNA hybrids, as they have high Tms that necessitate elevated reaction temperatures. In a perfectly matched hybrid, the Tm may depend on a variety of conditions. Some conditions include ionic strength, the concentration and presence or absence of monovalent cations, base composition of the oligonucleotides, the size of the oligonucleotides, the annealing properties including the amount of mismatches present and the presence of any denaturing agents. For instance, the Tm increases 16.6 degrees Celsius for a one fold increase in monovalent cations between 0.01 and 0.40 M NaCl. Also, for 25 mers, single base deletions show a decrease in Tm by 10 degrees Celsius. For every mismatch the Tm is lowered by 5 degrees Celsius. Denaturing agents such as urea reduce the Tm of a duplex in solution by approximately 30 degrees Celsius.

FIG. 4 shows a series of melting curves with the addition of urea to complementary strands of DNA in solution. The figure shows a plot of % single stranded DNA vs. temperature. Melting curves are shown for 25 mer, 60 mer, and 60 mer with denaturant. The solid lines in the diagram indicate the hybridization temperatures after the denaturant urea is added to the sample. It should be noted that the temperature for optimal duplex formation is generally 5–10 degrees below the Tm. Maximum rates of hybridization are achieved at temperatures 20–25 degrees Celsius below the Tm (the temperature at which the strands of a double-stranded probe are half dissociated) (MARMUR, J. G. and DOTY, P. J., Mol. Biol., 3, pp. 584, 1961). Hybridization temperatures at the probe Tm proceed very slowly. For longer probes, hybridization should be carried out at 65–68 degrees Celsius. However, this temperature is detrimental to the micro array surface. Buffer modifiers such as urea significantly reduce the effective Tm for duplex DNA by 15–30 degrees Celsius, enabling annealing to single stranded probes on the micro array surface to occur. This is particularly important for micro array surfaces, where high temperatures are detrimental to surface stability. A Tm modifier, for example, 50% formamide, is capable of reducing the Tm of a nucleic acid hybrid so that hybridizations can be carried out at 35-42 degrees Celsius. The advantages of using formamide-based hybridization buffers for nylon membrane hybridizations is that probes are more stable at the lower temperatures and there is better retention of non-covalently bound nucleic acids on the membrane. Formamide has no effect on hybridization rate when used in the range of 30–50% (Howley, P. M., et al, J. Biol. Chem., 254, pp. 4876, 1979). The figure clearly shows that as the denaturant is added to the oligonucleotides in solution, the hybridization temperature is dropped below the original melting temperature. This is ideal for use in micro arrays, because less energy is then needed to heat the system to get maximum hybridization. Secondly, since lower heat is applied and the temperature is lowered there are less denaturing effects on the actual oligonucleotide strands. Also, although the Tm of the 60 mer is higher than the 25 mer, the addition of denaturant still lowers the Tm and hybridization temperature.

The invention provides a solution to be used with the arrays 2. The solution contains a chemical moiety having the formula:

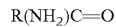

where R is $NH_2$ or $CH_3$. In one embodiment of the invention R is an amino group (the resulting compound is urea). In a second embodiment R may be an alkyl group (if R=$CH_3$, the resulting compound is acetamide). The case where R is a hydrogen atom is excluded (when R=H, the resulting compound is formamide, and the toxicological properties of the compound are very different). Suitable ligands may also include alkyl, substituted alkyl, aryl, substituted aryl, aralkyl, substituted aralkyl, and their derivatives.

Each of the above embodiments of the invention may be used with a solution that may be added to arrays 2 or other process or apparatus that allows for the hybridization of a nucleotide, biopolymer, or similar type component in a reaction solution or mixture.

Denaturant Buffer Optimization

Tests were conducted in order to achieve hybridization optimization with various denaturants. In addition, although short (20–25 base) oligonucleotides should theoretically provide the greatest discrimination between related sequences, observation by others have shown that short oligonucleotide lengths provide poor hybridization properties (Guo et al., 1994; Shchepinov et al., 1997). For these reasons, studies were conducted to maximize hybridization efficiency at longer lengths such as the 60-mer. These longer oligonucleotides or biopolymers have the advantage of more closely resembling the solution state with enhanced hybridization properties (Guo et al., 1994; Lockhart et al., 1996; Shchepinov et al., 1997).

In order to achieve optimal sensitivity and specificity of hybridization of 60-mer oligonucleotide arrays to complex target cRNA, a reduction of the Tm of the oligonucleotide and target is required. In other words, the length of the oligonucleotide requires added amounts of heat or energy to obtain hybridizations. However, this added energy or the level required for complete hybridization often requires levels of heat or energy that can simultaneously destroy the same biopolymers that are desired to hybridize.

Denaturant Study Structure

Grids experiments were designed using a 3×3×2×2 construction optimized for hybridization on the metric of "Mean Specificity" (mean specificity is defined in the equation that follows) as a function of probe length (20 to 60-mer). Tests were conducted using 3, 4, 4.92 M urea at various temperatures including 40, 45, and 50° C. Results were duplicated and dye swapped pairs were used to control for any Cy3 vs. Cy5 channel bias (defined as + or – polarity). Mean specificity is given as the average over all the probes of a given length to a given gene (GCN4=Yel009C).

Samples and Labeling

Samples were labeled with fluorescent dyes (Cy3 and Cy5) for hybridization studies. The specific target used included a pure labeled GCN4 antisense RNA. Cross-hybridization targets included an amplified (polyA+-specific) labeled GCN4/GCN4 yeast knockout (KO) total RNA. In each experiment the (+) polarity was the Cy3 labeled specific target and the Cy5 labeled KO target. The (–) polarity was the Cy5 labeled specific target and the Cy3 labeled KO target. Data from each of the polarities was combined in the dye swap pairs. Dye swaps were performed to eliminate experimental and channel bias.

Specific Signal vs. Probe Position (GCN4)

Specific signal and probe position are highly correlated. Previously it has been shown that hybridization efficiency is dependent on probe position. Probes designed closer to the 3' end of the corresponding gene give higher signal intensities due to the nature of the enzyme transcriptase activity. In addition, signal strength increases as probe length increases and frequency of good probes increases as probe length increases. These factors were important to consider in the study.

Cross-hybridization Problem

Cross-hybridization is a problem in hybridization experiments. Increased hybridization stringency decreases cross-hybridization problems in annealing experiments. Therefore, various parameters must be tested in order to arrive at maximum sensitivity and specificity with a denaturant. In other words, we want the ideal conditions and concentrations to produce effective hybridizations below the Tm of a biopolymer and target. The problem with such experiments being that specificity (most effective correct binding) to sensitivity (maximum signal detection) are not easily achieved. In other words, optimal specificity may be achieved at a different stringency than optimal sensitivity. For formamide, optimal specificity has been observed for at a formamide concentration of approximately 4× that for optimal sensitivity. The KO mutant protocol was employed for comparisons to pure cross-hybridization signals. An optimization metric was employed to quantify mean specificity. The mean specificity can be given by the equation:

$$Specificity = \frac{\overset{+Polarity}{\max(Ssig, Smin)_{g,i}} + \overset{-Polarity}{\max(Ssig, Smin)_{r,i}}}{\max(Xsig, Smin)_{g,i} + \max(Xsig, Smin)_{r,i}}$$

Where, $Ssig$ is SPECIFIC SIGNAL $Xsig$ is CROSS HYB SIGNAL $Smin = 2.6 \, \sigma_{Background}$ $$MeanSpecificity = 1/N \sum_{i=1}^{N} Specificity$$

Observed Optima for Various Probe Lengths and Temperatures (Urea as a Denaturant)

FIG. 5 shows a contour plot of the observed optimal conditions using urea concentrations with varying probe lengths. Urea concentrations from 2.5 to 5.5 M are plotted on the x-axis and probe lengths were tested from 10 to 70-mers using similar targets. The optimum ridge shows the optimal conditions for hybridization with the addition of the denaturant at 50° C. The ideal is a denaturant concentration that provides the greatest effect on the varying probe lengths when the temperature is held constant. The ridge represents this area on the contour plot. No optimal urea concentrations were bracket (area that is encircled in diagram) for longer probes at 40 or 45° C. The optimal urea concentrations bracketed were at 50° C. for a probe length (L=30, 35, 40 45, 50 and 55). No optimal urea concentration was bracketed at 50° C. for L=60. However, the results were extrapolated using the optima for other lengths.

FIG. 6 shows the optimal urea concentrations of 50° C. probe length series. The plot shows average GCN4 specificity plotted against urea concentration. Each of the curves is concave down with a maxima around 4.0 M urea concentration. The curves in each case are parabolic and show predictable trends.

FIG. 7 shows the extrapolated optimal urea concentration for a probe length of 60-mer at a temperature of 50° C. Optimum urea concentration at 50° C. is plotted against probe length. Probe length is graphed from 25 to 65-mer. For the 60-mer the optimal urea concentration is predicted to be between 5.1 and 5.3 M.

FIG. 8 shows a contour plot of the extrapolation to predicted optimum for the probe having a length of 60. Probe length has been plotted against urea concentration. The ridge in the diagram shows the optimum predicted for the denaturant on the prescribed conditions. The diagram shows that the optima for these experiments are very broad.

Therefore, denaturants added to a probe and target can be very effective in lowering Tm for improved hybridizations. Maximum urea concentration being approximately 4.92 M.

FIG. 9 shows the results of the Cy3 and Cy5 labeled micro arrays. The diagram shows the effects of oligonucleotide length and hybridization stringency on hybridization to yeast genes. Three yeast genes are shown: YDR345C (HXTT3), YER0109W (ISC1) and (GCN4) are tiled on a DNA oligonucleotide micro array. The oligonucleotide probes corresponding to each of the three yeast cDNAs are of increasing length, 20, 25, 30, 35, 40, 45, 50, 55, 60-mer, and have been tilted along the gene, spaced three oligonucleotides apart and arrayed in a 75 rows×195 column format. Reverse gray images reveal hybridization of oligonucleotides probes in 4.92 M urea at 40° C. Cy4 labeled Yeast GCN4 KO cRNA (2 μg), highlites HXT3 probes on the array. Whereas PCR amplified Cy3 labeled full length GCN4 DNA (0.5 ng) highlites GCN4 probes. Probes hybridizing equally to Cy5 and Cy3 are labeled yellow. ISC1, in the middle of the array, is a no-expressing gene. The diagrams clearly show that hybridization takes place at lower temperature with the added denaturant. Similar hybridizations can be seen in the low and high temperature micro arrays. However, the higher temperatures show slight problems with delamination, while the lower temperature graphs show an absence of such problems. For an example of the solution(s) used in the experiments see Tables 1–3. Table 1 is the general buffer system. Table 2 shows a solution to be employed in the Table 1 preparation.

The invention also provides a kit for using the composition. The kit provides for hybridizing biopolymers at temperatures below their standard hybridization temperatures. The kit comprises a micro array; a composition for use with the micro arrays, a target for detection and an optional set of instructions. The optional set of instructions may describe how to use the denaturant to obtain most effective binding hybridization temperatures. The micro array may be constructed of any number of probe lengths. The target may be a known or unknown biopolymer. The composition includes the chemical component $R(NH_2)C=O$ where R is an amino or an alkyl group. The chemical component may be used alone or in solution.

Having described the composition and kit of the present invention, a brief description of the method is now in order. The method includes the application or use of the same chemical composition. The composition may or may not be in a buffered solution. The method allows a probe to hybridize to a target at a temperature lower than their standard hybridization temperature. The steps of the method comprise adding to the probe and target a chemical component of the formula: $R(NH_2)C=O$ where R is an amino or an alkyl group, heating the probe and target in the presence of the added component, and then allowing the probe and target to hybridize.

EXAMPLE 1

Micro Arrays

Spotted cDNA arrays. Robotically deposited arrays of PCR products, each corresponding to a single yeast ORF, were as previously described (Marton, M. J. et al., 1998).

Oligonucleotide arrays. Surface-bound oligonucleotides were synthesized essentially as proposed (Blanchard et al., 1996). Hydrophobic glass wafers (75×75 mm) containing exposed hydroxyl groups for nucleotide coupling were prepared using a self assembling silane mixture to form a uniform, hydrophobic surface with a controlled density of hydroxyl groups extending by a single methylene unit above unfunctionalized silane components (S. M. Lefkowitz et al, unpublished data). Phosphoramidite monomers in propylene carbonate were delivered to defined positions on the glass surfaces using commercial ink-jet printer heads. Synthesis cycles were otherwise similar to traditional oligonucleotide synthesis, with the exception that capping was omitted. After manufacture, arrays were diced to 25×75 mm to accommodate commercial scanners.

EXAMPLE 2

Oligonucleotide Selection for Micro Arrays

*Saccharomyces cerevisiae* oligonucleotide set design were constructed as described below. Sequences were chosen from the full genome sequence (obtained from http://genome-www.stanford.edu/Saccharomyces). All 60-mer sequences with the 3' kb of nuclear encoded ORF sequences were evaluated. First, low-complexity sequence was masked using RepeatMasker (University of Washington and Genetic Information Research Institute). Second probes with 35–45% (G+C) were taken. Among these, a set of oligonucleotides overlapping by <40 bases was derived and analyzed by BLAST (http://www.ncbi.nlm.nih.gov/BLAST/) to identify those with lowest similarity to other source sequences. The eight remaining probes with the highest predicted specificity were selected to represent the source sequence. In some cases, eight oligonucleotides meeting these criteria were not identified, in which case selection stringencies were lowered and/or fewer than eight oligonucleotides were printed.

Human oligonucleotide sets were designed as described below. A total of 49,218 Homo sapiens sequences were picked from the longest messenger RNA (mRNA) sequences representing UniGene clusters (Release 111, 15 Apr., 1999) (http://www/ncbi.nlm.nih.gov/UniGene/). For each sequence, every 60-mer between 50 and 350 bases from the 3' end of the sequence was evaluated. First, oligonucleotides were filtered to remove with any repeat elements. Simple repeats or repeat elements were detected using Repeat Masker. Oligonucleotides with homopolymeric stretches of more than six bases were also rejected. Second, oligonucleotides were filtered to be <50% G and 25–70% (G+C). Among those remaining, a set of oligonucleotides overlapping-by <30 bases was derived and analyzed by BLAST to identify those with lowest similarity to all other source sequences. The surviving oligonucleotide with the highest predicted specificity was selected to represent its source sequence. The 23,965 oligonucleotides on the array used are those among 49,218 with the highest signal intensity when hybridized with cRNA prepared from Jurkat cells.

Mutations and deletions were performed as described below. Mismatch bases were "mutated" at random, for example, a mutated guanine had an equal possibility of mutation to each of the other possible bases (adenine, cytosine, or thymidine). In the case of deletions, additional sequence adjacent on the synthetic mRNA was added so that a total of 60 complementary bases was retained. For each number of randomly placed single-base mismatches or deletions, 110 different oligonucleotides were designed. For sequential mismatches, each position was represented by a single oligonucleotide sequence printed on five different spots.

EXAMPLE 3

Cell Culture

Saccharomyces cerevisiae cultures were grown as described (Marton et. al., 1998). The gcn4Δ/gcn4Δ strain is R1792; the hxt3Δ/hxt3Δ strain is R5918. Strains that are often used and profiled are prototrophic diploid (i.e. R1165). NB4 cells (human promyelocytic leukemia) were obtained from the American Type Culture Collection (Rockville, Md.). Human cell lines were grown in RPMI medium supplemented with 10% fetal bovine serum in an atmosphere of 5% $CO_2$.

EXAMPLE 4

RNA Isolation

Yeast total RNA was isolated by phenol:chloroform extraction and poly-A purified as described (Marton et al., 1998). Human total RNA was isolated using TRIzol (Life Technologies, Rockville, Md.) or Rneasy (Qiagen, Valencia, Calif.).

EXAMPLE 5

Synthetic cRNA and mRNAs

Full length S. cerevisiae ORFs GCN4 and HXT3 were amplified by PCR from a genomic DNA template and ORF specific primers. The T7 RNA polymerase (T7RNAP) promoter sequence was introduced into the antisense primer for each ORF. ORF specific cRNAs were then produced from the DNA templates by in vitro transcription using a kit well know in the art (MegaScript, Ambion, Austin Tex.). After labeling (as described below), these synthetic cRNAs were used directly for micro array hybridization. The array was hybridized with a mixture of 2 μg Cy3-labeled cRNA from a GCN-4 deficient strain of S. cerevisiae and 0.5 ng Cy5-labeled GCN4 ORF-specific IVT product (cRNA) (~4.5 copies per cell of the 843 nt GCN4, ORF, assuming ~15,000 transcripts per S. cerevisiae and an average transcript length of 1 kb). For spike-in RNAs, a portion of the adenovirus type 5 Ela (nucleotides 560–972) was amplified by PCR from a full-length plasmid clone of the gene and subcloned into the pS64Poly(A) Vector (Promega, Madison, Wis.). Random 60-mer oligonucleotides were then cloned into Xbai/BamHI sites of this subclone, adjacent the poly-A sequence. Individual clones were isolated, and the sequences of the inserts determined. To generated synthetic mRNAs, clones were linearized with EcoRI and an SP6 IVT reaction was then performed. This reaction was then followed by DNase treatment of the product. Synthetic mnRNAs were purified on Rneasy columns (Qiagen).

EXAMPLE 6

MRNA Reverse Transcription and Amplification

In vitro transcription (IVT) was performed as modified (DeRisi, et al., 1997). Total RNA was used as input for cRNA synthesis. An oligo-dT primer containing a T7 RNA polymerase promoter sequence was used to prime first strand cDNA synthesis, and random hexamer were used to prime second stranded cDNA synthesis by Maloney murine leukemia virus (MMLV)RT. This reaction yielded a double stranded cDNA that contained the T7 RNA polymerase promoter at the 3' end. The double stranded cDNA was then transcribed into cRNA by T7RNAP.

PCR-coupled IVT (PCR-IVT) was performed as described below. 3' end cDNA was synthesized by an adaptation of the protocol of Zhao et al. (Zhao et al., 1998). To prevent transcript detection biases due to unequal amplification of certain sequences during PCR, the amount of input RNA was increased to 2.4–4.0 μg and decreased the number of PCR cycles to 10. To allow further sequence amplification by cRNA synthesis, a T7RNAP promoter sequence was added to the 3'-end primer sequence used during PCR. Following PCR, amplified DNA was isolated by phenol/chloroform extraction and used as a template in an IVT reaction (MegaScript Ambion).

EXAMPLE 7

Sample Labeling, Hybridization, Scanning and Image Analysis

Different cDNA and cRNA were labeled with Cy3 and Cy5 dyes using a two step process. First, allylamine-derivitized nucleotides were enzymatically incorporated into cDNA or cRNA products. For cDNA labeling, a 1:1 mixture of 5-(3-aminoallyl) thymidine 5'-triphosphate (Sigma) and thymidine triphosphate (TTP) was used in place of TTP during cDNA synthesis. For cRNA labeling, a 1:3 mixture of 5-(3-aminoallyl)uridine5'-triphosphate (UTP) was substituted for UTP in the IVT reaction. Allylamine derivatized cRNA or c DNA products were purified using commercial columns. Columns were washed 3× with 80% ethanol and eluted with water. Purified products were reacted with N-hydroxy succinimide esters of Cy3 or Cy5, following the manufacturer's instructions. Dye molecules were separated from labeled products using standard commercial columns. Cy3 labeled cRNA or cDNA from "control" cells were mixed with the same amount of Cy5-labeled product from "experiment" cells (~30 μg for cDNA or 5 μg for cRNA per human sample per hybridization, unless otherwise noted). All hybridizations were done in duplicate and fluor reversal, to compensate for biases cause by differing chemical properties of the fluorescent dye molecules as well as for biases associated with normalization. Before hybridization, labeled cRNAs were fragmented to an average size of ~50–100 nt before incubation at 60, 50, 45, or 40 degrees Celsius for 30 minutes in the presence of 10 mM $ZnCl_2$, cDNAs or fragmented cRNAs were added to hybridization buffer as described below. Hybridizations were carried out in a final volume of 3 ml in a flexible plastic enclosure at 40 degrees Celsius on a rotating platform in a hybridization oven (Robbins Scientific, Sunnyvale, Calif.). After hybridization for 16–24 hours, slides were washed (rocking ~30 s in 6×SSPE, 0.005% sarcosine, then rocking 30 s in 0.06× SSPE) and scanned using a confocal laser scanner (General Scanning, Wilmington, Mass.; Genetic Microsystems, Woburn, Mass.; or Axon, Foster City, Calif.). Fluorescence intensities on scanned images were quantified, corrected for background and normalized (Marton et al., 1998).

EXAMPLE 8

The Solution or Reaction Mixture

Table 1–3 shows a description and breakdown of the components used in a reaction solution. The components generally include nuclease free water, 5 M MCl (M=$Na^+$, $Li^+$, or other suitable monovalent cation), 1.0 M M-MES, pH=6.4, and 10% w/v Sarcosine (sigma L-9150). The volumes for each of the components are shown in the tables for the case where M=Na$^+$. Solutions may be altered and components changed. The guiding design principle is that the addition of the urea, amide, or an amino component allows for hybridization of the polynucleotide or biopolymer on the micro array surface at lower temperature than the standard hybridization temperature without the addition of the denaturant. The optimization of the chosen temperature and the composition of the hybridization buffer represents a balancing of the stabilization of perfect Watson-Crick nucleic acid duplexes and the destabilization of imperfect duplexes, i.e. the balance between sensitivity and specificity. [NOTE: optimal hybridization is usually achieved at a temperature about 5° C. below the melting temperature of the desired duplex. Melting temperature is effected by monovalent cations (usually Na$^+$ or Li$^+$) concentration, probe length, probe sequence, modifier concentration and target concentration. The affect of the modifier (urea, acetamide, etc.) is to lower the melting temperature, all other factors being equal, by destabilizing the hydrogen bonding of Watson-Crick base pairs. −pKw].

EXAMPLE 9

Effects of Various Molarities on Oligonucleotide Hybridization Temperature

FIGS. 5–9 show the effects of various urea molarities on the polynucleotide or biopolymer hybridization temperature. As can be seen in the figures, higher amounts of urea are effective in lowering hybridization temperatures. Note that as the probe length increases, there is also a higher required molarity of urea to obtain the maximum or most effective hybridization temperature.

For further questions regarding any of the procedures in the described examples see (Hughes et al., 2001).

TABLE 1

| Hybridization Title: | GCN4 Experiment Protocol |
|---|---|
| Dye swap Polarity | (−) |
| Array Design File | Scerevisiae__hxt3__yer019w__gcn4__20–60mers.txt |
| Total Number of slides/Temp/Treat | 2 |
| Final Volume per slide: | 3000.0 μl |

| | [Component] | 4.92 M Urea Volume | Amount | Final [Component] |
|---|---|---|---|---|
| RNA FRAGMENTATION STEP | | | | |
| nuclease-free water | 100.0% | 110.0 μl | | 3.7% |
| GCN4 spike (S. Cerevisiae) Cy5 | 0.10 μg/ml | 10.20000 | 0.5 ng | 0.00017 μg/ml |
| gcn4 KO (S. Cerevisiae) Cy3 | 339.30 μg/ml | 11.85 μl | 2 μg | 0.67 μg/ml |
| Random 25-mer | 10.00 mg/ml | 60.00 μl | | 0.10 mg/ml |
| 25 mM Zn(OAc)$_2$, 975 mM Tris, pH 7.6 | 25x | 8.00 μl | | 1.0x |
| Fragmentation volume: | 100.00 μl | 200.0 μl | | |
| 0.5 M EDTA POST-fragmentation stop volume | 5.00 μl | 10.00 μl | | |
| Total Fragmented Volume: | | 210.00 μl | | |
| HYBRIDIZATION STEP | | | | |
| Fragmented sample volume per tube: | | 210.0 μl | | |
| Urea Volume Concentrate (8M Urea) | | 3690.0 μl | | 4.92 M Urea |
| 20/7x Hyb Buffer Concentrate | | 2100.0 μl | | 1x |
| Water | | 0.0 μl | | |
| Total | | 6000.0 μl | | |

TABLE 2

Desired Volume (ml): 25
20/7x (2.86x) Urea Hyb. Buffer

| Component | [Component] | Volume (ml) | 2.86x Concentrate | Final [Component]/2.86x (in hyb. chamber) |
|---|---|---|---|---|
| nucleose-free water | 100.0% | 2.71 | 10.9% | 3.8% |
| 5M NaCl (nuclease-free) | 5.0M | 14.29 | 2.9M | 1.0M |
| 1.0M Na-MES, pH 6.4 | 1000.0 mM | 3.57 | 142.9 mM | 50.0 mM |
| 0.5M EDTA (pH 8.0) | 500.0 mM | 0.86 | 17.1 mM | 6.0 mM |
| 10% w/v Sarcosine (Sigma L-9150) | 10.0% | 3.57 | 1.4% | 0.5% |
| Total | | 25.0 ml | | |

TABLE 3

Desired Volume (ml): 10
2x QC2-3 Hyb. Buffer

| Component | [Component] | Volume (ml) | 2x Concentrate | Final [Component]/2x (in hyb. chamber) |
|---|---|---|---|---|
| nuclease-free water | 100.0% | 0.23 | 2.3% | 1.15% |
| 8M LiCl (nuclease-free) | 8.0M | 1.53 | 1.224M | 0.612M |
| 0.5M Li-MES, pH 6.1 | 500.0 mM | 6.00 | 300.0 mM | 150.0 mM |
| 0.5M EDTA (pH 8.0) | 500.0 mM | 0.24 | 12.0 mM | 6.0 mM |
| 15% w/v Lithium Dodecyl Sulfate, | 15.0% | 2.00 | 3.0% | 1.5% |
| 10% Triton X-100 | | | | |
| Total | | 10.0 ml | | |

We claim:

1. A method that allows a probe and target to specifically hybridize at a temperature lower than their standard hybridization temperature, comprising:
   (a) heating the probe and target in the presence of a chemical component of the formula:

R(NH$_2$)C=O where R is an amino or a methyl group; and
   (b) allowing the probe and target to hybridize,
   wherein said probe is an oligonucleotide probe covalently linked the surface of a microarray.

2. A method as recited in claim 1, wherein said probe and target are heated to a temperature that is lower than their standard hybridization temperature.

3. A method as recited in claim 1, further comprising adding said chemical compound to a solution prior to heating step (a).

4. A method that allows a probe on a micro array surface to specifically hybridize to a target at a temperature lower than their standard hybridization temperature, comprising:
   (a) heating the probe and target in the presence of a chemical component of the formula:

R(NH$_2$)C=O where R is an amino or a methyl group; and
   (b) allowing the probe and target to hybridize,
   wherein said probe is an oligonucleotide probe covalently linked to the surface of a microarray.

5. A method as recited in claim 4, wherein said probe and target are heated to a temperature that is lower than their standard hybridization temperature.

6. A method as recited in claim 4, further comprising adding said chemical compound to a solution prior to heating step (a).

7. A method as recited in claim 1, wherein said chemical component is urea.

8. A method that allows a probe and target to hybridize at a temperature lower than their standard hybridization temperature, comprising:
   (a) heating the probe and target in the presence of acetamide; and
   (b) allowing the probe and target to hybridize,
   wherein said probe is an oligonucleotide probe attached to the surface of a glass substrate.

9. A method for detecting nucleic acids using a microarray, comprising:
   contacting a sample comprising labeled nucleic acids with an addressable microarray of oligonucleotide probes covalently linked to a surface of a glass substrate in a hybridization buffer comprising urea; and
   detecting labeled nucleic acids that specifically hybridize to said oligonucleotide probes.

10. The method of claim 9, wherein said contacting is done at a hybridization temperature of about 50° C.

11. The method of claim 9, wherein urea is present in said hybridization buffer at a concentration of about 5M.

12. The method of claim 9, wherein urea is present in said hybridization buffer at a concentration of about 4M.

13. The method of claim 9, wherein said oligonucleotides are 60-mer oligonucleotides.

* * * * *